United States Patent
Hammer et al.

(10) Patent No.: US 6,753,959 B2
(45) Date of Patent: Jun. 22, 2004

(54) OPTICAL SHUTTER FOR SPECTROSCOPY INSTRUMENT

(75) Inventors: Michael R. Hammer, Sassafras (AU); Martin K. Masters, Rowville (AU); Stewart R. Campbell, Forest Hill (AU); Peter G. Layton, Hampton Park (AU)

(73) Assignee: Varian Australia Pty LTD, Mulgrave (AU)

( * ) Notice: Subject to any disclaimer, the term of this patent is extended or adjusted under 35 U.S.C. 154(b) by 273 days.

(21) Appl. No.: 09/958,448

(22) PCT Filed: Feb. 15, 2001

(86) PCT No.: PCT/AU01/00147

§ 371 (c)(1), (2), (4) Date: Oct. 5, 2001

(87) PCT Pub. No.: WO01/61291

PCT Pub. Date: Aug. 23, 2001

(65) Prior Publication Data

US 2004/0085535 A1  May 6, 2004

(30) Foreign Application Priority Data

Feb. 15, 2000 (AU) .............................................. PQ5653
Aug. 8, 2000 (AU) .............................................. PQ9273

(51) Int. Cl.[7] .................................................. G01J 3/28
(52) U.S. Cl. ..................................... 356/330; 359/245
(58) Field of Search ................................ 356/326, 330; 359/245

(56) References Cited

U.S. PATENT DOCUMENTS

| 4,214,835 A | * | 7/1980 | Roos | 356/306 |
| 5,412,468 A | * | 5/1995 | Lundberg et al. | 356/326 |
| 5,781,331 A | * | 7/1998 | Carr et al. | 359/288 |

FOREIGN PATENT DOCUMENTS

EP  0 366 847 A2 * 9/1990 ............ G02B/26/08

* cited by examiner

Primary Examiner—F. L. Evans
Assistant Examiner—Kara E. Geisel
(74) Attorney, Agent, or Firm—Edward H. Berkowitz

(57) ABSTRACT

Spectroscopy apparatus for spectrochemical analysis of a sample having an excitation source (60) for providing spectral light (62) of the sample for analysis. The spectral light (62) is analysed via an optical system (64–66–68) that includes a polychromator (70, 74–80) and solid state multielement array detector (82). The elements (i.e. pixels) of the detector (82) are serially reel by means (84) to provide light intensity measurements as a function of wavelength. A problem is that the elements (pixels) of the detector (82) continue to accumulate change during the serial read-out. This is avoided by providing an optical shutter (72) for blocking the spectral light (62) whilst elements (pixels) of the detector (82) are being serially read. Shutter (72) has a piezoelectric actuator which is preferably a bimorph mounted as a cantilever. It is preferably located adjacent to the entrance aperture (70) of the polychromator. Bimorph structures for the actuator and drive and protective circuit arrangements are also disclosed.

20 Claims, 7 Drawing Sheets

OPTICAL SHUTTER FOR SPECTROSCOPY INSTRUMENT

FIELD OF THE INVENTION

The present invention relates to a shutter for blocking the path of a light beam in a spectroscopy instrument.

BACKGROUND

It is known that chemical analysis of samples can be accomplished by a variety of spectroscopy-based techniques. For example, the amount of various chemical elements in a sample can be ascertained by optical emission spectrometry or by atomic absorption spectrophotometry. The concentration of various chemical species in a sample can be ascertained by ultraviolet-visible absorption spectrometry or infrared absorption spectrophotometry, or by ultraviolet-visible fluorescence spectrophotometry. These are only a few examples of spectroscopy-based chemical analysis techniques.

Equipment for spectroscopy-based chemical analysis typically operates by measuring the intensity of light either as a function of wavelength or at one or more specific wavelengths. This may be done with a monochromator and a single detector collecting intensity data for each wavelength of interest in a serial fashion, but it is also possible to collect light intensity data for more than one wavelength simultaneously. Because of the greater time efficiency offered by simultaneous measurement, this approach is increasingly favoured for practical applications.

Modem simultaneous spectroscopic measurement apparatus typically includes an optical polychromator together with a solid state electronic detector device incorporating an array of optical sensor elements. The detector can be, for example, a charge-transfer device such as a charge-injection device (CID) or a charge-coupled device (CCD). A polychromator that is able to disperse the light in two dimensions (for example an echelle polychromator) can be employed, in which case a 2-dimensional array of optical sensor elements can be used with advantage as a detector. Alternatively a polychromator that provides dispersion in one dimension only (such as a single-grating-based polychromator) can be utilised, and a linear array detector used. The 2-dimensional approach offers better wavelength resolution for a given wavelength range and so is favoured for chemical analysis applications, particularly for elemental analysis by optical emission spectrometry.

Elemental analysis typically involves operation at optical wavelengths extending from the visible to the far ultraviolet, which places limitations on the types of detectors that can be used. Solid state detectors of various types are known to be suitable for this application, for example charge transfer devices, both CIDs and CCDs, are known to be useful. An example of such a detector is the CCD detector disclosed by Zander et al. in U.S. Pat. No. 5,596,407. This has a number of optically sensitive sites, generally referred to as pixels, that are distributed in a precise geometric arrangement over the surface of the detector to map accurately the optical image from the polychromator. Each optically sensitive site or pixel is capable of converting the energy of incoming light to free electrons, which are stored at the optically active site. The number of electrons, and thus the total charge, accumulated within each pixel will depend on the light intensity incident on that pixel and the time for which the pixel is exposed to said light, said time being usually referred to as the integration time.

Measuring the optical intensity therefore involves determining the amount of charge built up over a known integration period. In order to do this it is necessary first to collect the charge and then to transfer the charge accumulated at each pixel to appropriate readout electronics.

Two principal ways of carrying out this process are available. The first, used in the detector disclosed by Zander et al. in U.S. Pat. No. 5,596,407, duplicates each optically active pixel with an optically inactive pixel. The first step in the readout process is a parallel transfer operation that transfers the charge from each row of active pixels to the corresponding row of inactive pixels. The charge is then stepped through these inactive pixels as the shift register nodes. The second approach uses the optically active pixels themselves as shift register nodes, so that with each move operation the charge on every pixel moves to the next pixel along, with the charge of the last pixel moving to the readout circuit.

Both approaches have their attendant advantages and disadvantages. The second approach has the advantage that most of the surface area of the CCD can be covered by active pixels, thus maximising the light sensitivity of the whole device. It also avoids the need for any secondary structure. That is, this approach provides more efficient utilisation of available light in spectroscopic applications. It also permits the use of relatively inexpensive, off-the-shelf detectors.

The disadvantage of the second approach is that the pixels continue to accumulate electrons generated by any incoming light during the readout process. As a consequence, as the charge from one pixel moves through other pixels on its way to the readout circuitry, it accumulates additional charge, the amount of which depends on the light intensity incident at each of those other pixels and the speed of charge transfer. This has the effect of smearing the resultant image data, which is totally unacceptable in a spectroscopy application. To overcome this disadvantage it is proposed to provide an optical shutter that can block all light to the detector during the readout process.

Known optical interrupters for use in spectroscopic or photographic applications generally comprise one or more metal vanes driven by electromagnetic actuators. For example such devices are disclosed by Vincent in U.S. Pat. No. 3,427,576, U.S. Pat. No. 3,595,553 and U.S. Pat. No. 3,664,251, by Fletcher et al. in U.S. Pat. No. 3,804,506, by Saito et al. in U.S. Pat. No. 4,290,682 and by Krueger in U.S. Pat. No. 6,000,860. These mechanisms are relatively large, and consequently rather slow. This is a serious limitation in spectroscopic applications. The devices also tend to consume significant amount of power. Because of the number of moving parts the reliability and lifetime of this type of mechanism is uncertain. Furthermore, devices offering sufficiently long life tend to be relatively expensive.

Hikita et al. disclose in U.S. Pat. No. 5,268,974 an optical switch based on a piezoelectric bimorph. The use of a piezoelectric device is advantageous because such devices are silent, and they can be operated reliably for many millions of cycles. They are relatively inexpensive. They dissipate very little power and thus do not cause any significant local rise in temperature within the optical system of an instrument. Any such local rise in temperature is undesirable because it may lead to thermal expansion and consequent optical drift. Hikita et al disclose an optical switch having an optical shielding element at the free end of a cantilevered piezoelectric bimorph such that a light beam travelling parallel to the length of the bimorph is either intercepted by said optical shielding element or allowed to pass, depending on the polarity of the voltage applied to the bimorph. Light that is allowed to pass falls on a mirror close to the fixed end of the cantilevered bimorph and is reflected from said mirror and detected by an optical detector. The invention of Hikita et al. is suitable for use with narrow, well-collimated beams of light, such as laser beams, but it would not be suitable for the light beams in spectroscopic instruments. Such beams, although very narrow at certain points, converge rapidly towards such points and diverge rapidly away from them. This is a consequence of the need to capture as much light as possible from the spectroscopic source and transfer it to the detector. A light switch according to the teachings of Hikita et al. in U.S. Pat. No. 5,268,974 would not be suitable for use with a widely convergent or divergent beam because the device itself would partially obstruct the beam irrespective of the position of the optical shielding element. This would cause an undesirable loss of light transmission efficiency.

The discussion of the background to the invention herein is included to explain the context of the invention. This is not to be taken as an admission that any of the material referred to was published, known or part of the common general knowledge in Australia as at the priority date established by this application.

SUMMARY OF THE INVENTION

According to the invention there is provided spectroscopy apparatus for spectrochemical analysis of a sample comprising a light source and a system for interacting the light source and a sample for providing spectral light of the sample, and an optical system including a polychromator and a multi-element solid state detector for providing intensity measurements of the spectral light as a function of wavelength, means for serially reading a plurality of the elements of the detector to provide said light intensity measurements, and further including a shutter device having a piezoelectric structure, the shutter device being operable on application of an electrical signal to the piezoelectric structure for movement between two positions, wherein at one position the spectral light is permitted to reach the detector, and at the other position the spectral light is prevented from reaching the detector for the plurality of detector elements to be serially read while the detector is shielded from the spectral light.

In a preferred embodiment the piezoelectric structure is a bimorph which is preferably in the form of a cantilevered strip, but the invention is not limited to this construction.

The light source may be adapted to receive a representative portion of an analytical sample and to heat this portion to a temperature sufficient to decompose it and to excite spectrochemical emission of light from molecules, atoms or ions resulting from the decomposed portion, for example as in atomic emission spectrometry. Alternatively light from the source may be passed through a decomposed sample portion and its absorption at particular wavelengths measured, for example as in atomic absorption spectrophotometry. Other techniques encompassed by the invention include passage of light through a suitably presented sample and measurement of its absorption at particular wavelengths (for example as in ultra-violet-visible absorption spectrometry, or infrared absorption spectrophotometry), or measurement of emitted light at particular wavelengths (for example as in fluorescence spectrophotometry). The wording herein of interacting a light source and a sample for providing "spectral light of the sample" is intended to encompass all of these and other similar spectrochemical analysis techniques involving the measurement of the intensity of resultant light as a function of wavelength.

The detector will normally be a charge transfer device (CCD or CID) that may be made up of a plurality of detector elements (or pixels) arranged, for example, in a regular array of rows and columns.

A shutter device in spectroscopy apparatus according to the invention can meet the relatively demanding attributes required of it in spectroscopic elemental analysis applications. Specifically, it can have very low attenuation (possibly zero attenuation) when open and can be arranged to block the spectral light beam completely when closed. It can operate with light extending into the far ultraviolet region of the spectrum and not degrade in the presence of intense UV light such as that emitted by the plasma sources typically used for elemental analysis by emission spectrometry. Since the operation of the shutter determines the integration time, the switching time between open and closed positions (or vice versa) may be short, in order to achieve short integration times. It is also accurately repeatable. The optical shutter device, being based on the use of a piezoelectric actuator, also has a long life. For example, a preferred embodiment has been subjected to over 30 million cycles without failing. The complete shutter device can be made relatively small offering further advantages given that space inside an optical system of a spectroscopy instrument is often limited. A shutter device according to the invention may also be manufactured relatively inexpensively.

In a preferred embodiment a shutter element for blocking the spectral light beam is attached to a piezoelectric structure in the form of a bimorph at or adjacent to its free end. This shutter element may be any stable, sufficiently rigid and optically opaque material having a low mass. In a preferred embodiment, the shutter element is a piece of thin metal foil.

In operation, the movement of the bimorph places the shutter element between the source of a light beam and an entrance aperture through which said light beam must pass if the detector is to be exposed to light. The size of the shutter element is such that there can be no direct path for light to enter the entrance aperture when the shutter is in its closed operating position. For more complete exclusion of light from the entrance aperture, it is also necessary to prevent light entering the entrance aperture by indirect paths. In particular, it is preferable to exclude the possibility that light passing the shutter and striking the surface surrounding the entrance aperture might be reflected or scattered from said surface onto the surface of the shutter element and then be reflected or scattered therefrom into the entrance aperture. Accordingly, it is preferable that the surface surrounding the aperture, and the surfaces of the shutter element, be treated (for example to make it matt black) to reduce reflection and the scattering of incident light. Furthermore, to achieve an even greater reduction of the possibility of light entering the shutter by indirect means it is a possible further aspect of this invention to place a mask, having an opaque surface and an aperture, between the shutter element and the source of the light beam so that the only light approaching the shutter is that corresponding to the effective optical entrance beam of the polychromator. The function of such a mask is to prevent the direct passage of light past the shutter element to the surface surrounding the entrance aperture. To further reduce the possibility of light entering the entrance aperture by indirect routes, it is a further possible aspect of this invention that a second mask, having an opaque surface and an aperture, be placed between the shutter element and said first mask. Said second mask is arranged in such a manner that when the shutter element is so placed as to block the entrance aperture there can be no direct path between the aperture of said first mask to the surface surrounding the entrance aperture.

The amount of movement required of a bimorph actuator of a shutter device according to the invention to prevent light from reaching the detector depends on the place at which the blocking occurs. Typically the entrance aperture to the polychromator of a spectroscopic instrument of the invention is quite small and if the light beam is blocked close to the entrance aperture the amount of movement required will be correspondingly small. A peak-to-peak movement of about 0.5 mm would suffice. Embodiments of a shutter device having a cantilevered bimorph actuator as described hereinabove can provide peak to peak motions of about 0.6 mm.

The piezoelectric structure or actuator of the invention bends in response to an applied electric voltage and the motion thus does not involve bulk movement, as is required in known mechanical interrupters. Such bending is responsive to the electrical drive signal and follows the applied voltage rapidly, providing fast operation. Electrically, a piezoelectric bimorph, which is the preferred form for the actuator, resembles a capacitor and it has low static dissipation and low loss when switching. Since there are few parts and no rotating or sliding surfaces there is no wear and the lifetime is dependent only on the life of the piezoelectric bimorph actuator. Such actuators have long lifetimes if operated within their specified ratings and if driven with a suitable applied voltage versus time regime.

The characteristics of the voltage versus time profile applied to drive the shutter device are determined primarily by the requirement that the shutter be driven quickly from one extreme of its movement to the other, with minimal oscillation at each end of its travel. Oscillation is excessive if it results in multiple interruptions of the light, including partial interruptions. In order that the shutter may be driven from one extreme of its movement to the other as quickly as possible while keeping oscillations to acceptable levels, an additional preferred feature of the invention is the application of an appropriate voltage versus time profile to the bimorph.

Several voltage versus time regimes have been investigated by the inventors, each having its attendant advantages and disadvantages. In the first of two applied voltage versus time regimes included within the scope of this invention, the applied voltage versus time profile causes the shutter first to commence its movement towards its operated position and then to decelerate it so that it reaches its operated position with substantially zero velocity. This has the advantage of allowing rapid movement of the shutter element. It has the disadvantage that the required rapid changes of the applied voltage can cause stresses in the bimorph that can lead to the partial fracture of the piezoelectric material and consequent failure of the device. To avoid this, in the second of the applied voltage regimes included within the scope of this invention the voltage versus time profile applied to the bimorph is such that at no time is the cantilevered bimorph subject to forces that would tend to accelerate it to velocities in excess of those corresponding to its natural frequency of vibration. Application of such forces can cause distortion of the bimorph, or the excitation of higher-order vibrations, and these can lead to the fracture of the piezoelectric material. Depending on its extent such fracture may or may not prevent the movement of the shutter, but it can result in the movement being unacceptably different from that intended.

A disadvantage of the second voltage versus time regime is that the speed of movement of the shutter cannot be greater than that set by the natural frequency of vibration of the bimorph. Where the utmost speed is not required it is preferable to use the second voltage versus time regime and so avoid the risk of damage to the device. Accordingly, the invention preferably encompasses electrical circuit means for applying a voltage versus time regime such that the cantilevered bimorph is not subjected to forces that would tend to accelerate it to velocities in excess of those corresponding to its natural frequency of vibration. A particular example is the use of an electrical circuit to drive the bimorph quasistatically. Such an arrangement keeps the voltage applied to the bimorph close to the equilibrium voltage as the bimorph moves. Stresses and higher order vibrations in the bimorph are thereby kept to a minimum.

Mechanical resonance of the cantilevered bimorph would result in simple harmonic motion. A plot of the position of the free end of the bimorph as a function of time would be a sine wave. Preferably, the voltage applied by the drive circuit mimics this wave shape to drive the bimorph efficiently and with the minimum of stress. Preferably, a lockout is provided in the circuit so that once a movement is commenced it must be completed before a movement in the opposite direction is initiated.

In the practical application of the invention it may be that the power supplies to the drive circuit are unstable for a brief period when they are switched on or off. Such instability could result in fast-changing voltages being applied to the bimorph, resulting in fracture of the piezoelectric material as described previously. Accordingly, it is an additional preferred feature of this invention to provide protection circuitry to prevent such fast-changing voltages being applied to the bimorph. An example of such protection circuitry is the provision of a high resistance element that can be placed in series with the bimorph. Since the bimorph acts as a capacitor, such an arrangement will sufficiently limit the rate of rise of a voltage applied to the bimorph. In a preferred embodiment of the invention, a microprocessor supervisory device monitors the levels of the supply rails to the driving circuit. When all levels are within specification it bypasses the series resistance element, thus providing fast drive to the bimorph as required for normal operation. The bypassing of the series resistance is preferably done relatively slowly, thus ensuring that the bimorph is not subjected to any abrupt changes in the drive voltage as the drive circuit impedance is reduced. In a preferred embodiment the bypassing of the series resistance is done by a photovoltaic relay. Any drop in the voltage on the supply rails below specified levels results in the photovoltaic relay being turned off quickly, thus interposing the resistance and filtering any fast transient drive signals that would otherwise be applied to the piezoelectric bimorph.

The time taken for the shutter to fully obstruct the spectral light beam when the appropriate voltage for that movement is applied has been found by the inventors to be highly reproducible for a particular shutter device. Likewise, the time taken for the shutter to be fully clear of the light beam when the appropriate voltage for that movement is applied is also highly reproducible for a particular shutter device. When different specimens of the shutter device were tested, however, it was found that these times, while highly consistent for each specimen, varied to a small but significant extent from one specimen to another.

Given the spectroscopic field of this invention, it may be desirable in some applications to vary the integration time by varying the time for which the shutter is open. It is often preferable to take multiple readings at short integration times to avoid the detector being saturated by long exposure to intense spectral lines from elements present in the sample at relatively high concentrations. It is also necessary that measurements made by summing the results of multiple readings at a short integration time should yield the same analytical results as would be obtained by the use of one long integration time, said long integration time being equal to the product of the number of readings and the length of said short integration time. Accordingly, it is necessary to take account of the variability, from one device to another, in the time taken for the shutter to fully obstruct the light beam when the appropriate voltage for that movement is applied, and of the time taken for the shutter to be fully clear of the light beam when the appropriate voltage for that movement is applied. It would be possible to provide adjustment means to set these times to the same values for each device, but this would be complex and expensive. It is preferable to conduct a calibration procedure such as, for example, that taught by Dr Tim Abbott of the Canada-France Hawaii Telescope (now at the Nordic Optical Telescope, Canary Islands, Spain) for calibrating mechanical shutters for CCD detectors on astronomical telescopes.

As explained by Dr Abott, the shutter delay pattern can be deduced by comparing a long exposure flat field with an exposure in which the shutter has been opened and closed many times. The counts in pixel i in an image where the shutter has been opened and closed once are given by:

$$I_{1,i}=(t_1+s_i)F_i$$

where $t_1$ is the reported exposure time of the image, $S_i$ is the total shutter delay at pixel i, and $F_i$ is the number of counts detected per second at that pixel.

If the shutter is opened and closed n times before the CCD is read out, then the counts at pixel i will be:

$$I_{2,i}=(t_2+ns_i)F_i$$

where $t_2$ is the reported exposure time for this second image and it has been assumed that the shutter delay is the same for every open-close cycle.

Since $F_i$ is the same for both images, the shutter delay at each pixel in the image can be deduced from the following:

$$S_i=(t_1 I_{2,i}-t_2 I_{1,i})/(nI_{1,i}-I_{2,i})$$

Another aspect of the invention provides a shutter device for blocking the path of a light beam in a spectroscopy instrument for preventing the further accumulation of charge by an optically sensitive detector of the instrument during a read time period for the detector following a charge accumulation time period, the shutter device including a piezoelectric structure which is a bimorph actuator in the form of a strip that is mounted as a cantilever to provide a free end, wherein the free end moves upon application of a driving voltage to the bimorph to block or unblock a light beam which propagates in a direction substantially at right angles to the plane of movement of the free end of the bimorph.

To better understand the invention and to show how it may be carried into effect, embodiments thereof will now be described by way of a non-limiting example only, with reference to the accompanying drawings.

DETAILED DESCRIPTION OF THE EMBODIMENTS

Figure 1:
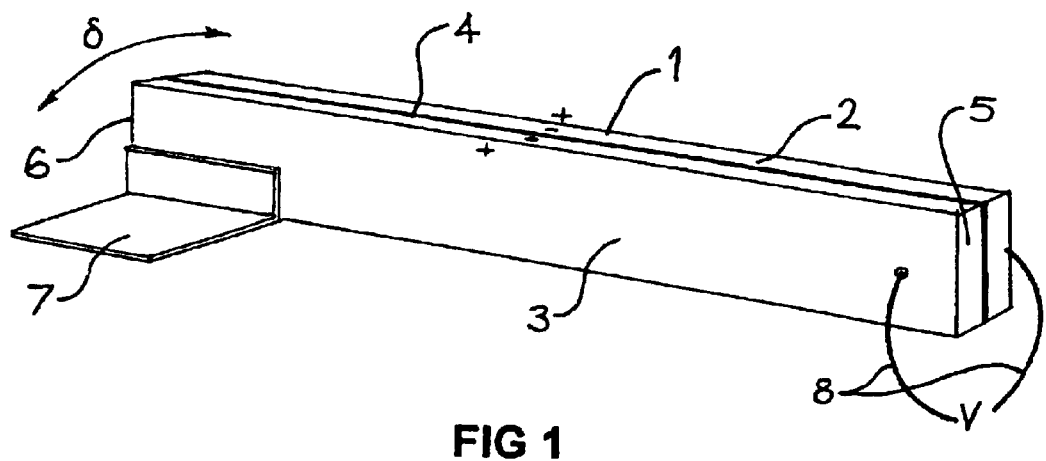
FIG. 1 is a diagram of an optical shutter according to an embodiment of the invention.
Figure 2:
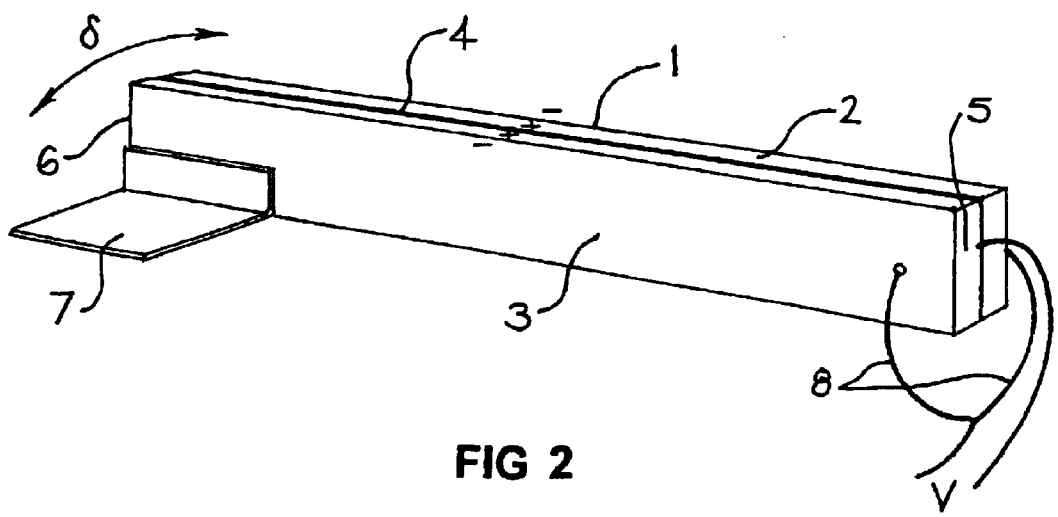
FIG. 2 shows an alternative shutter arrangement to that of FIG. 1.

A shutter of this invention employs a bimorph actuator 1 comprising two thin piezoelectric strips 2,3 brought into face-to-face engagement with their engaging faces bonded together or to opposite sides of a thin flexible electrically conductive substrate 4 as shown in FIG. 1. The strips 2 and 3 are made of a material having a high piezoelectric constant, for example lead zirconate titanate. If the two strips 2 and 3 are so arranged that the two negative poled faces (or the two positive poled faces) are bonded together, or on opposite sides of a thin flexible electrically conductive substrate 4 and connected electrically, then when a voltage V is applied across the outer faces through wires 8 one strip will increase in length while the other will decrease in length. Alternatively, the two strips 2, 3 can be bonded with a negative poled face bonded to a positive poled face either directly or on opposite sides of a thin flexible electrically conductive substrate 4 (see FIG. 2) and a voltage V applied between both outer faces and the bonded faces to obtain an equivalent effect. This effect causes the bonded bimorph strip 1 to bend, and when supported as a cantilevered beam at one end 5 the displacement obtainable at the unsupported free end 6 is substantial by piezoelectric standards. As an example, a bimorph actuator 1 which is 3 mm wide, 0.5 mm thick and with a cantilever length of 25 mm can achieve a peak-to-peak displacement δ of about 0.5–0.8 mm. Thus there is provided a small, simple robust and inexpensive actuator that can directly achieve the required displacement. The thin flexible electrically conductive substrate is preferably a carbon-fibre composite. To achieve the shuttering effect, a small piece of thin metal foil 7 or other appropriate material is glued or otherwise bonded adjacent to the free end 6 of the bimorph actuator 1 to act as a shutter element, blocking or unblocking the light path to a CCD detector in a spectroscopic instrument depending on movement of the free end 6 from a first position to a second position dependent upon the polarity of the applied drive voltage V.

Figure 3:
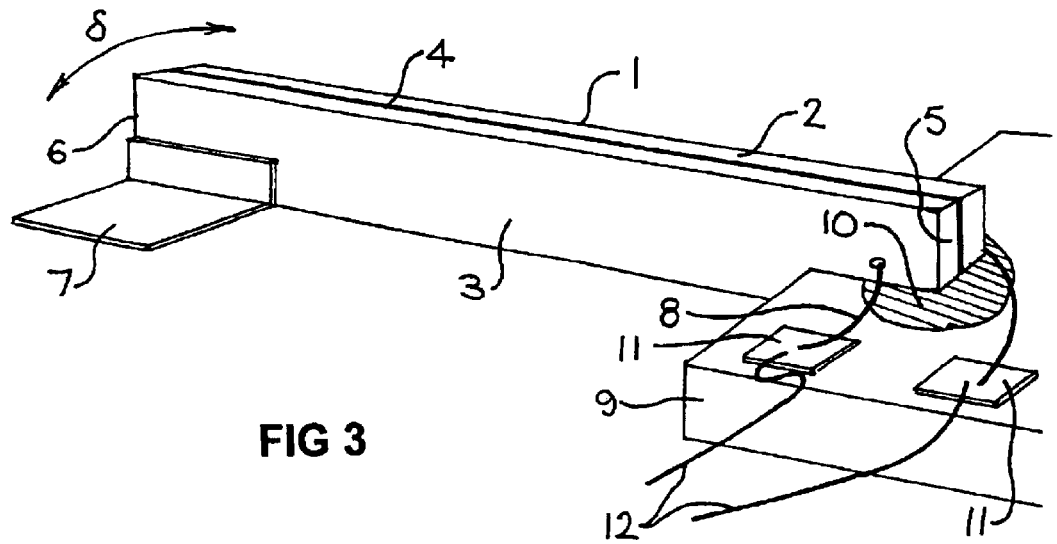
FIG. 3 shows a mounting and electrical connection arrangement for incorporating the shutter of FIG. 1 or FIG. 2 into a spectroscopic instrument.

FIG. 3 shows one possible means of mounting piezoelectric bimorph actuator 1 and making electrical connections to it. Bimorph 1 is attached to a fibreglass circuit board 9, being inserted into a slot in said circuit board and secured therein with epoxy cement 10 or other appropriate adhesive. Circuit board 9 is attached in position onto the entrance aperture of the polychromator or other spectroscopic apparatus (not shown). Electrical connection to bimorph 1 is established by means of connecting wires 8 that are soldered to copper contact pads 11 on board 9. Electric wires 12 are soldered to pads 11 for connection to a drive circuit such as that of FIG. 4.

Figure 4:
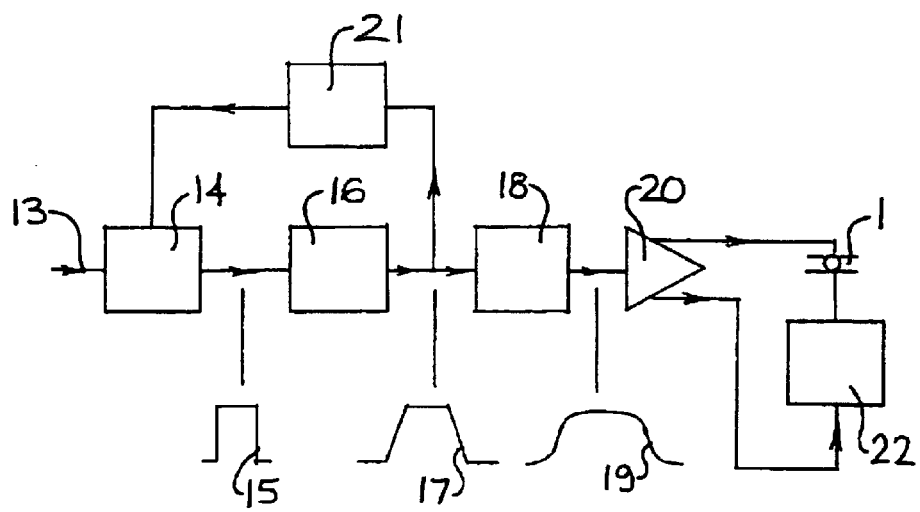
FIG. 4 is a schematic diagram of an electrical circuit arrangement suitable for driving the shutter of FIG. 1 or FIG. 2.
Figure 5:
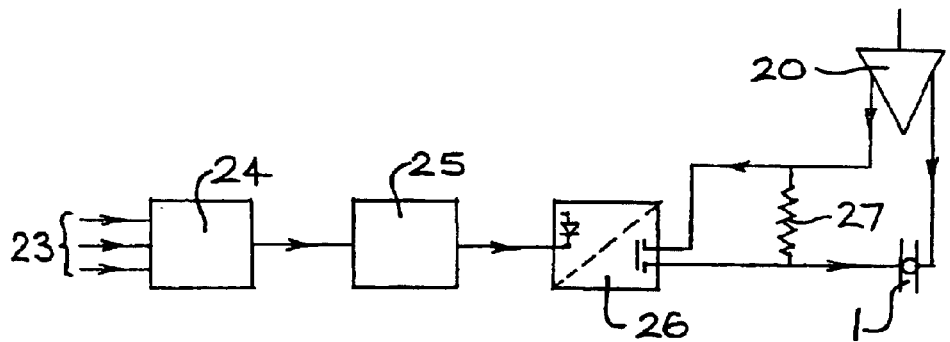
FIG. 5 is a schematic diagram of an electrical circuit arrangement to protect the piezoelectric bimorph of a shutter from rapid changes of voltage during start-up or shut-down.

The circuit diagram of FIG. 4 and associated voltage versus time waveforms show how the required driving voltage waveform may be achieved. A pulse signal 13 applied to Schmitt trigger pulse squarer 14 produces a square wave 15 that passes to an integrator and limiter 16, producing a trapezoid wave 17. This passes to a sine shaper 18 and generates a quasistatic 'sine' wave 19, which is applied to amplifier 20. The output of amplifier 20 drives the piezoelectric bimorph actuator 1 to move the shutter to block (or unblock) the beam for a time determined by the width of pulse 19 and then return it to its original position. The output of differentiator 21 is fed into Schmitt trigger pulse squarer 14 as a lockout, so that once a movement of bimorph 1 is initiated, it must be completed before a signal is applied to drive it in the opposite direction. Protection circuit 22 is shown in more detail in FIG. 5. Referring now to FIG. 5, Voltages from supply rails 23 are monitored by microprocessor supervisory device 24. If any of these voltages fall below pre-determined specified levels, timing and relay drive 25 is activated. This switches photovoltaic relay 26 off quickly, so that the driving voltage from amplifier 20 is passed through high-value resistance 27 to ensure that bimorph 1 is not subjected to any abrupt changes in said driving voltage. When all supply voltages 23 return to their specified values the microprocessor supervisory device 24 signals the timing and relay drive 25 to close photovoltaic relay 26. Relay 26 is closed slowly, through the linear region of its operating characteristics, to ensure that there are no abrupt voltage changes applied to the bimorph 1.

Figure 6:
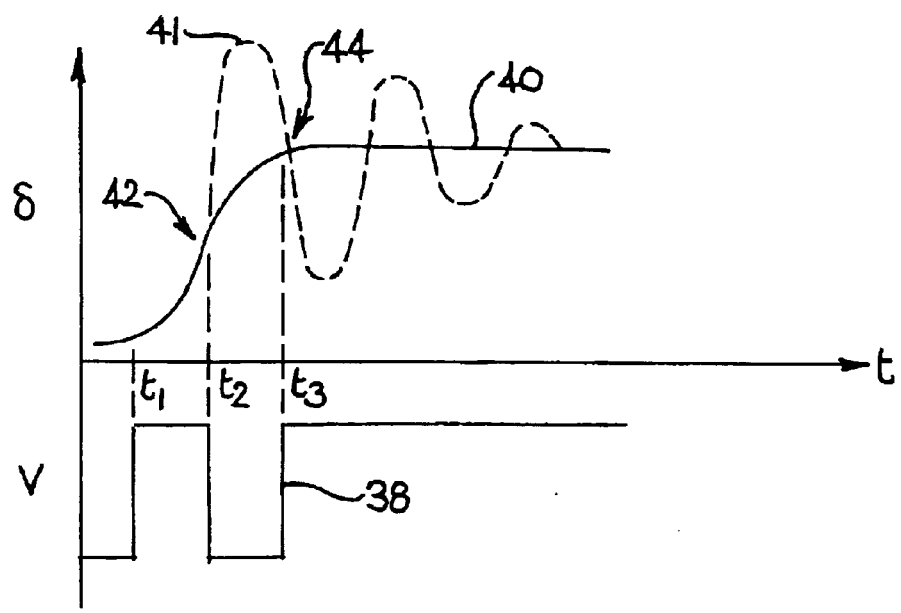
FIG. 6 is a graph showing a trace of drive voltage (V) and a trace of displacement (δ) against time (t) for a shutter of FIG. 1 or FIG. 2.
Figure 7:
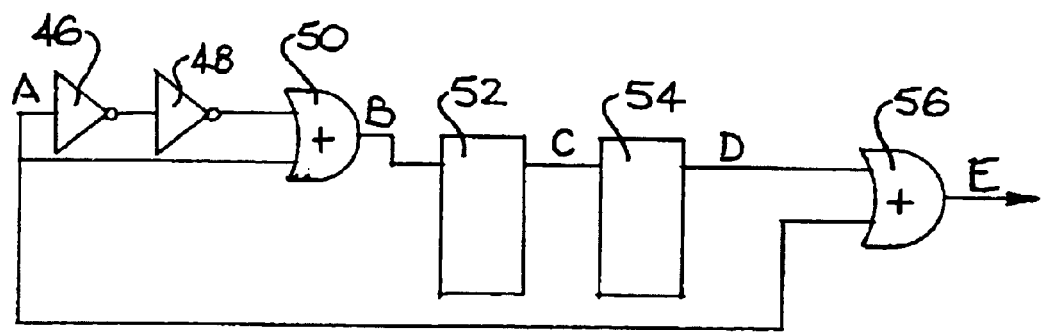
FIG. 7 is a schematic diagram of an alternative electrical circuit arrangement for driving a shutter of FIG. 1 or FIG. 2 for producing the displacement-time trace of FIG. 6.

An alternative piezoelectric excitation voltage sequence, as shown in FIG. 6, involves an initial application of the drive voltage V at time $t_1$ (see lower voltage (V) versus time (t) trace 38) until the bimorph 1 has moved through approximately half the desired displacement (eg. point 42 on upper displacement ($\delta$) versus time (t) trace 40). (The dashed trace 41 illustrates the decaying oscillation that an undamped bimorph 1 would experience on application of a single step voltage V). The polarity of the drive voltage is then reversed at time $t_2$ to actively decelerate the bimorph 1, so that it reaches the desired position with essentially zero velocity (eg. point 44 on upper trace 40). Finally, at time $t_3$, as the end 6 of the bimorph actuator 1 reaches the target position the steady state drive voltage is re-applied to maintain the new position. The displacement $\delta$ of the bimorph actuator 1 approximates much more closely to a step function, as the trace 40 in FIG. 6 shows. In practice, it has been found that the piezoelectric properties of a bimorph 1 are sufficiently constant from unit to unit and in repetition to allow the excitation drive timing to be established by independent timing elements such as monostables rather than via feedback of the bimorph position. The circuit diagram of FIG. 7 and associated voltage traces FIGS. 8A–E show how the required alternative excitation damping voltage waveform may be practically achieved. The circuit of FIG. 7 comprises inverters 46, 48, OR gates 50, 56 and monostables 52, 54. The traces A–E correspond to voltage versus time signals at the positions marked A–E on the circuit of FIG. 7.

Figure 8:
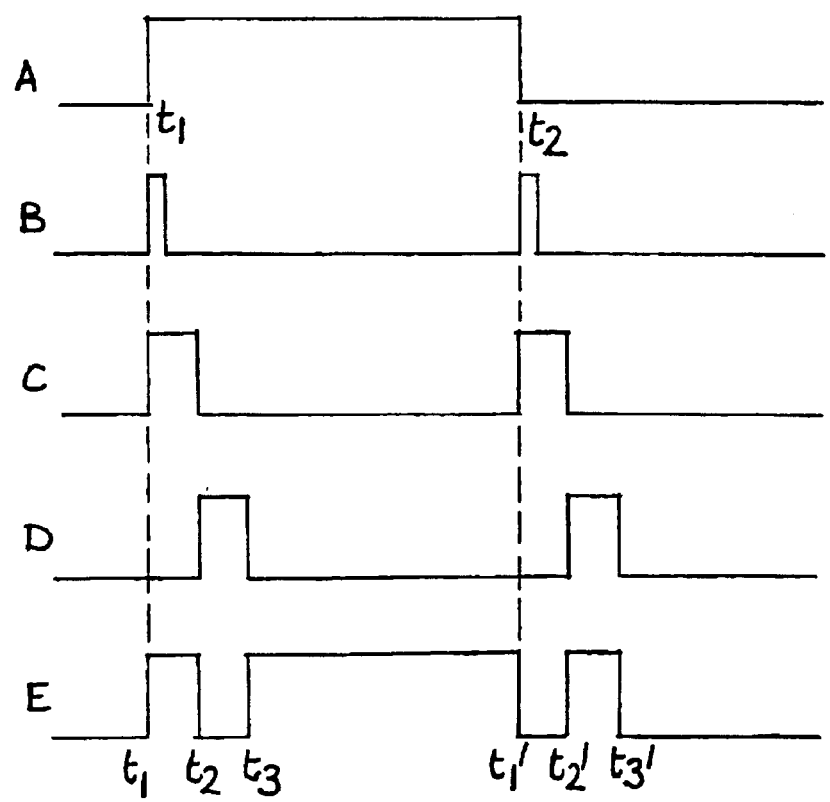
FIG. 8 shows voltage versus time signals from various locations A–E in the circuit of FIG. 7.

Trace A of FIG. 8 represents the applied drive signal to actuate the shutter device 1 between times $t_1$ and $t'_1$, whilst trace E of FIG. 8 denotes the actual drive to piezoelectric actuator 1, utilising the excitation sequence explained above. Monostable elements 52 and 54 provide the voltage switching periods as triggered by the applied drive signal A, the sequence $t_1$–$t_3$ showing the drive signal for actuating piezoelectric actuator 1 into its shuttering position, whilst the sequence $t_1$–$t_3$ represents the drive in the reverse direction for actuator 1 to recover its at-rest position.

Figure 9A:
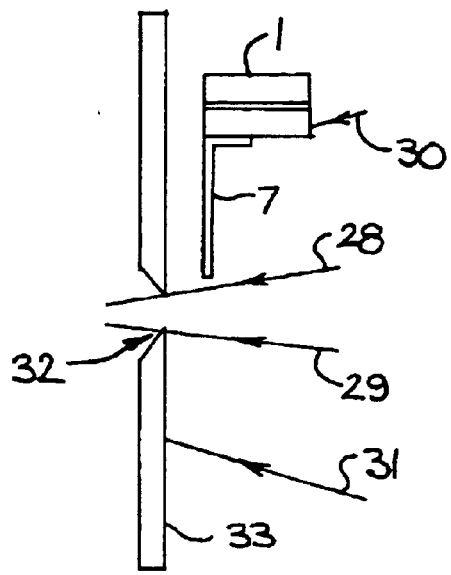
FIGS. 9A and 9B show how scattered or reflected light can bypass the shutter.
Figure 9B:
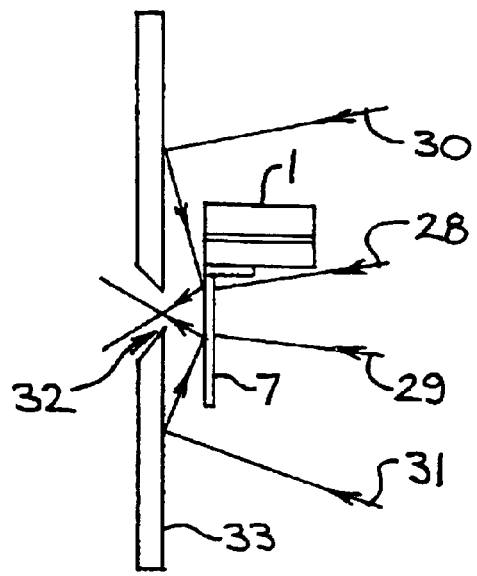

FIG. 9A shows the bimorph 1 in a first position in which light rays 28 and 29 are allowed to enter the entrance aperture 32 of a spectroscopic instrument (not shown). Rays 28 and 29 indicate the effective optical entrance beam of said spectroscopic instrument, while rays 30 and 31 indicate the edges of the beam from the light source (not shown) focussed onto the plane of entrance aperture 32. FIG. 9B shows bimorph 1 in a second position in which shutter element 7 prevents light rays 28 and 29 from entering entrance aperture 32, but rays 30 and 31 striking the surface 33 surrounding the entrance aperture 32 may be reflected or scattered from said surface 33 onto the proximate surface of shutter element 7 and thence into the entrance aperture 32.

Figure 10A:
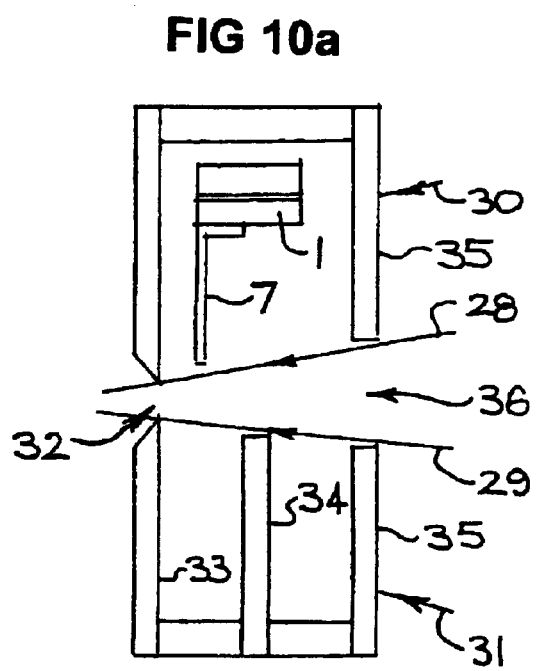
FIGS. 10A and 10B show how a mask arrangement placed between the shutter and the light source prevents scattered or reflected light from bypassing the shutter.
Figure 10B:
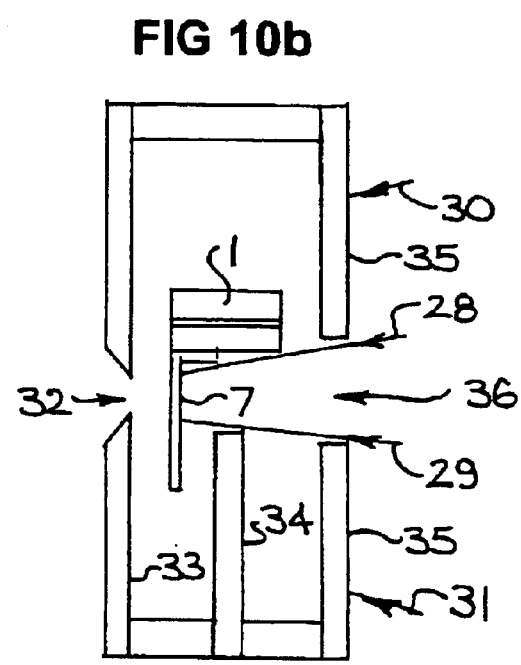

FIGS. 10A and 10B show how masks 34 and 35 placed between a source (not shown) of light rays 28, 29, 30 and 31 prevent light from striking the surface 33 around entrance aperture 32. Rays 28 and 29 indicate the effective optical entrance beam of a spectroscopic instrument (not shown), while rays 30 and 31 indicate the extreme edges of the light beam from said source focussed onto the plane of entrance aperture 32. Mask 35 includes an aperture 36 having a size just greater than that of the effective optical entrance beam at that location, said optical entrance beam being indicated by light rays 28 and 29. FIG. 10A shows the bimorph 1 in a first position in which light rays 28 and 29 are allowed to enter the entrance aperture 32 of a spectroscopic instrument (not shown). FIG. 10B shows bimorph 1 in a second position in which shutter element 7 prevents light rays 28 and 29 from entering entrance aperture 32, and at the same time rays 30 and 31 are prevented from striking the surface 33 surrounding the entrance aperture 32 by masks 34 and 35. Consequently the problem indicated in FIG. 9B of light entering entrance aperture 32 by reflection or scattering from surface 33 and the proximate surface of shutter 7 is avoided.

Figure 11:
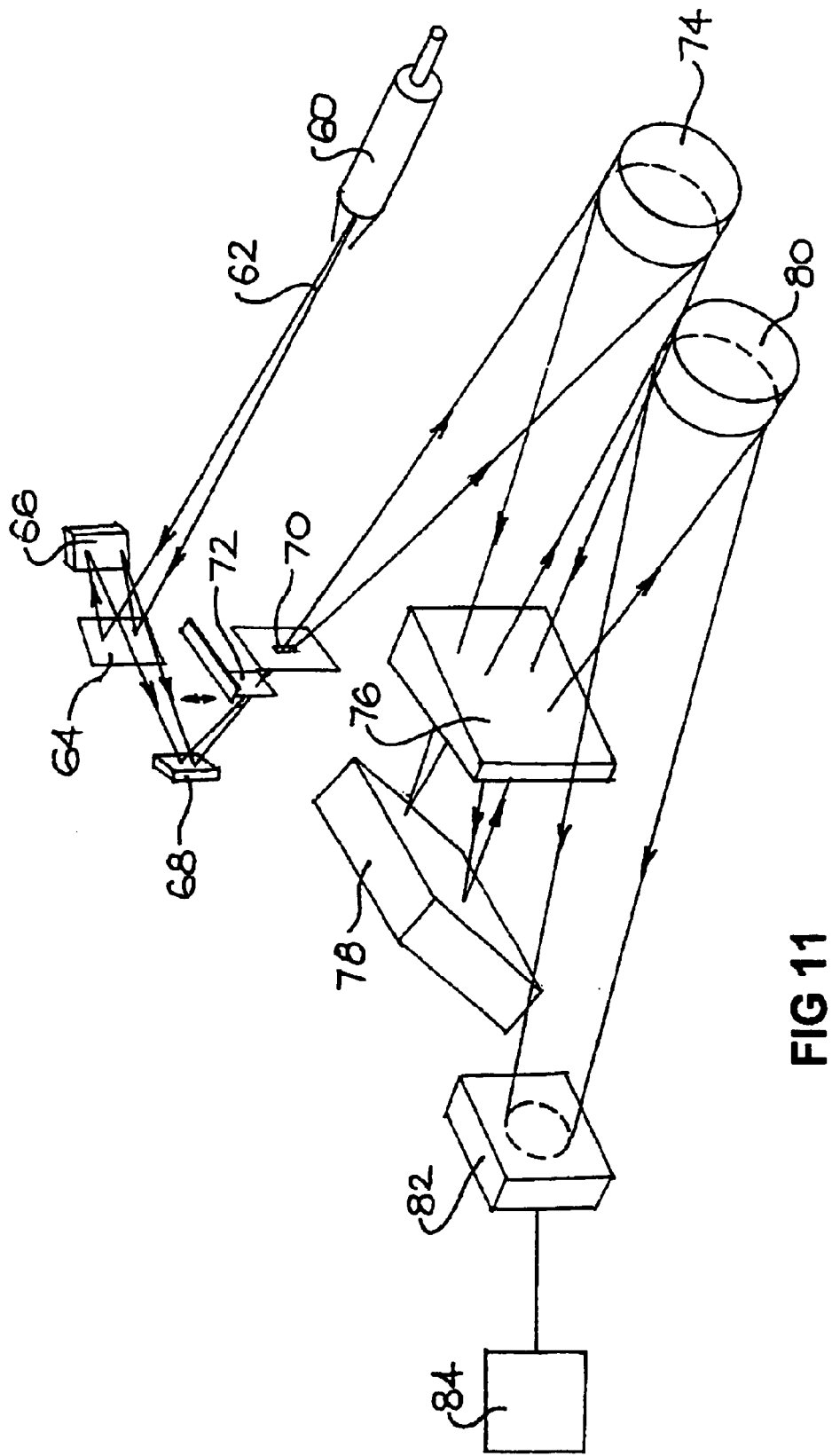
FIG. 11 schematically shows an optical emission spectrometer including an optical shutter according to the invention, and FIG. 12 schematically shows an absorption spectrometer including an optical shutter according to the invention.

An example of spectroscopy apparatus according to the invention, namely an optical emission spectrometer as illustrated by FIG. 11, comprises a spectroscopic light source 60 which emits spectral light of a sample 62. Light source 60 in a preferred embodiment is an inductively coupled plasma but may be any other spectroscopic light source adapted to emitting light of spectroscopic interest (i.e. spectral light of a sample).

Spectral light 62 emitted by spectroscopic light source 60 falls on mirror 64. Those skilled in the art will appreciate that it is advantageous that mirror 64 be provided with adjustment means (no shown so that light can be selected according to its spatial origin within spectroscopic light source 60. Spectral light 62 is reflected from mirror 64 onto a focusing mirror 66.

The spectral light 62 then strikes a folding mirror 68 and is thereby directed onto aperture 70, onto which it is focused by the action of focussing mirror 66. A shutter device 72 as above described is so located with respect to aperture 70 that the shutter 72 can selectively be moved to a first position in which it obstructs spectral light 62 or to a second position in which spectral light 62 passes without obstruction.

When shutter device 72 is in the second position the spectral light 62 passes through aperture 70 and falls on a first polychromator focussing mirror 74 which focuses the spectral light 62 through an order-separating prism 76 and onto an echelle grating 78. Light reflected from echelle grating 78 has been spatially separated in a first direction according to wavelength but a plurality of spectral orders are spatially superimposed, as is known to those skilled in the art. On passing through order-separating prism 76 the spectral light 62 is spatially separated in a second direction according to wavelength. The light 62 then strikes a second polychromator focussing mirror 80 which focuses it onto an array detector 82. An image of aperture 70 is formed on array detector 82 at a spatial position that is determined by the wavelength of the light. Array detector 82 is provided with a large plurality of light-detecting elements (pixels) that convert, by known means, incident light intensity into an electrical charge proportional to the intensity of the incident light.

Measurement of the electric charges generated at specific spatial positions on array detector 82 by means 84 for serially reading a plurality of elements of the detector 82 (which means is known) thus provides a measurement of the intensities of light of specific wavelengths. Such intensity measurements are converted to measurements of the concentration of specific chemical elements by reference to measurements made when samples having known concentrations of said chemical elements are subjected to the measuring process.

According to the invention, the shutter device 72 is operated by application of an electrical signal to its piezoelectric structure to move the shutter to the first position to prevent the spectral light 62 from reaching the detector 82. This allows a plurality of the elements of the detector 82 to be serially read by the means 84 whilst the detector 82 is shielded from the spectral light 62.

Thus FIG. 11 shows spectroscopy apparatus for spectrochemical analysis of a sample which comprises a light source and a system for interacting the light source and a sample 60 for providing spectral light 62 of the sample. The optical system of the spectroscopy apparatus includes a polychromator 70, 74–78 and the multi-element solid state detector 82. The apparatus also includes means 84 for serially reading a plurality of the elements of the detector to provide light intensity measurements.

Figure 12:
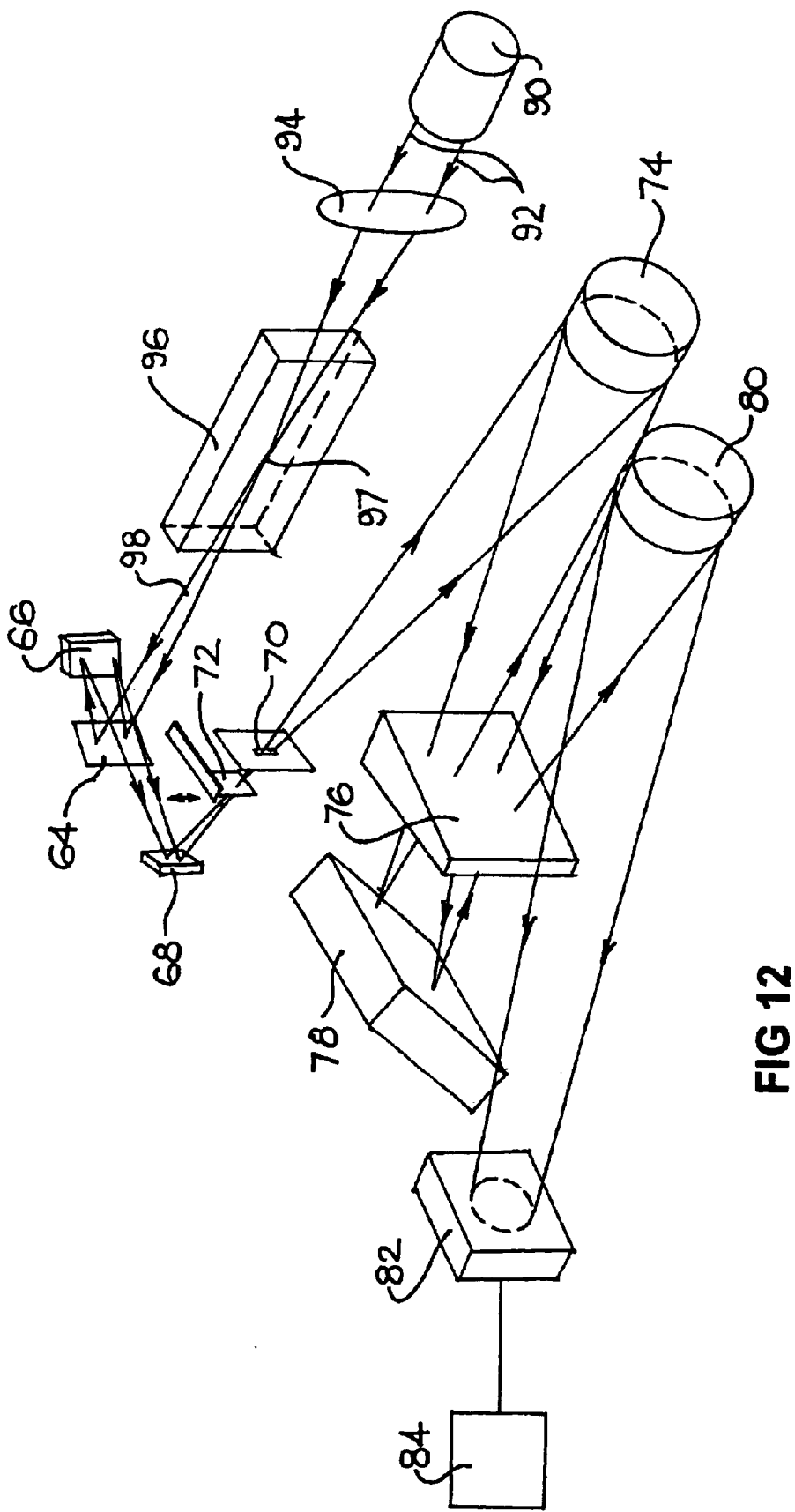

In an absorption spectrometer apparatus as illustrated by FIG. 12, light 92 is emitted by light source 90, which in a preferred embodiment is a hollow cathode lamp but which may be any other spectroscopic light source adapted to emitting light capable of being absorbed by a sample 98 in an absorption cell 96. Absorption cell 96 may be a chemical flame, a furnace, a glass cell, or any other device capable of containing a sample 97 of spectroscopic interest for exposure to light 92. The light 92 is focussed into absorption cell 96 by focussing means 94. Focussing means 94 may be a lens or a mirror or a plurality or combination thereof. For the purpose of obtaining information about the chemical composition of an analytical sample, a representative portion 97 of said sample is introduced into absorption cell 96 by means as known to those skilled in the art, and is therein caused to absorb light at specific wavelengths. The extent of absorption at specific wavelengths is indicative of the chemical composition of said sample. The light 98 exiting the absorption cell 96 is the spectral light of the sample as hereinbefore defined. Measurements of light absorption at specific wavelengths are converted to measurements of the concentration of specific chemical species of interest by reference to measurements made when samples having known concentrations of said chemical species are subjected to the measurement process.

The rest of the apparatus shown in FIG. 12 is the same as that shown in FIG. 11, and is therefore referenced by the same numerals. It separates the spectral light 98 into its constituent wavelengths and measures the intensity of said light 98 at wavelengths of interest, as hereinbefore described.

Measurement of the electric charges generated at specific spatial positions on array detector 82 provides a measurement of the intensities of light of specific wavelengths. Those skilled in the art will appreciate that such intensity measurements are readily converted to absorption measurements by reference to intensity measurements made when a sample containing essentially none of the chemical species of interest is placed in absorption cell 96.

The invention that has been described is applicable for use with various types of spectroscopic techniques such as, for example, optical emission spectrometry with an inductively coupled plasma source. It is also applicable to emission spectrometry with any other appropriate light sources including but not limited to electrical arcs, electrical sparks, plasma, glow discharges and flames. Furthermore, the invention is applicable to any spectroscopic apparatus or instrument that might require the rapid and reproducible blocking and unblocking of an optical path.

The invention has been described with reference to the use of a single shutter having a bimorph actuator serving to block and unblock an optical path, but clearly a number of such shutters may be used together and operable to block different optical paths or different parts of an image area.

The invention which has been described preferably makes the use of a piezoelectric bimorph arranged as a cantilever, in which the free end moves along an arc, but other configurations are possible. For example a piezoelectric bimorph might be configured as a simple beam, in which the centre of the beam moves up and down. In such a configuration the deflection is only 25% of that achievable from a beam of the same dimensions configured as a cantilever but the force exerted is 4 times greater. By way of another example, a piezoelectric bimorph might be configured as an 's' beam, in which the free end moves linearly. In such a configuration the deflection is only 50% of that achievable from a beam of the same dimensions configured as a cantilever but the force exerted is twice as great. Such alternative configurations are illustrated in the catalogue of a manufacturer of piezoelectric bimorphs (reference: Catalog #3, 1998, Piezo Systems, Inc., 186 Massachusetts Avenue, Cambridge, Mass., USA, page 33)

The invention described herein is susceptible to variations, modifications and/or additions other than those specifically described and it is to be understood that the invention includes all such variations, modifications and/or additions that fall within the scope of the following claims.

What is claimed is:

1. Spectroscopy apparatus for spectrochemical analysis of a sample comprising a light source and a system for interacting the light source and a sample for providing spectral light of the sample, and an optical system including a polychromator and a multi-element solid state detector for providing intensity measurements of the spectral light as a function of wavelength, means for serially reading a plurality of the elements of the detector to provide said light intensity measurements, and further including a shutter device having a piezoelectric structure, the shutter device being operable on application of an electrical signal of selected voltage versus time profile to the piezoelectric structure for monotonic movement between two positions, said voltage versus time profile first accelerating said shutter device toward one said position and then decelerates said shutter device such that it reaches the other said position with substantially zero velocity, wherein at one position the spectral light is permitted to reach the detector, and at the other position the spectral light is prevented from reaching the detector for the plurality of detector elements to be serially read while the detector is shielded from the spectral light.

2. Spectroscopy apparatus as claimed in claim 1 wherein the piezoelectric structure of the shutter device is a bimorph.

3. Spectroscopy apparatus as claimed in claim 2 wherein the bimorph is mounted as a cantilever having a free end which moves along an arc for said movement between said one and said another position.

4. Spectroscopy apparatus as claimed in claim 2 or claim 3 wherein the bimorph comprises two strips of piezoelectric material bonded to opposite faces of a flexible substrate.

5. Spectroscopy apparatus as claimed in claim 4 wherein the flexible substrate is a carbon-fibre composite.

6. Spectroscopy apparatus as claimed in claim 1 wherein the shutter device includes a shutter element affixed to the piezoelectric structure and which is moved by the piezoelectric structure to define said one and said another position whereat the shutter element blocks or unblocks said spectral light.

7. Spectroscopy apparatus as claimed in claim 1 wherein said movement of the shutter device defines a plane of movement and the arrangement of the optical system is such that said spectral light propagates substantially at right angles to said plane of movement.

8. Spectroscopy apparatus as claimed in claim 1 wherein the shutter device is positioned such that it blocks and unblocks the spectral light adjacent to an entrance aperture of the polychromator.

9. Spectroscopy apparatus as claimed in claim 8 including a mask positioned between the shutter device and the light source for allowing only spectral light corresponding to the effective optical entrance beam of the polychromator to reach the shutter device.

10. Spectroscopy apparatus as claimed in claim 9 including a second mask positioned between the shutter device and the first defined mask to prevent reflected spectral light from entering the entrance aperture of the polychromator when the shutter device blocks the spectral light.

11. Spectroscopy apparatus as claimed in claim 1 including an electrical circuit for supplying said electrical signal to the piezoelectric structure, the circuit providing said voltage versus time profile which accelerates the shutter device without subjecting it to forces that would produce velocities in excess of those corresponding to its natural frequency of vibration.

12. Spectroscopy apparatus as claimed in claim 11 wherein the voltage versus time profile is a quasi-static sine wave pulse having a width which determines the time period over which the piezoelectric structure is operated for the shutter device to either shield or unshield the detector.

13. Spectroscopy apparatus as claimed in claim 12 wherein the electrical circuit includes a lockout for ensuring completion of an initiated movement of the shutter device in one direction before a movement of the shutter device in the opposite direction is initiated.

14. Spectroscopy apparatus as claimed in claim 13 wherein the electrical circuit includes protective circuitry which prevents any transient voltages from being applied to the piezoelectric structure.

15. Spectroscopy apparatus as claimed in claim 14 wherein the protective circuitry includes a device for monitoring the electrical signal applied to the piezoelectric structure and a high resistance element, wherein the protective circuitry is operable for the high resistance element to be normally bypassed and for it to be interposed in series with the piezoelectric structure upon the sensing of a transient voltage by the monitoring device.

16. Spectroscopy apparatus as claimed in claim 1 wherein the multi-element solid state detector is a charge transfer device being a charge-injection device (CID) or a charge coupled device (CCD).

17. Spectroscopy apparatus as claimed in claim 16 wherein the elements of the detector are arranged as a regular array of rows and columns.

18. A shutter device for blocking the path of a light beam in a spectroscopy instrument for preventing the further accumulation of charge by an optically sensitive detector of the instrument during a read time period for the detector following a charge accumulation time period, the shutter device including a piezoelectric structure which is a bimorph actuator in the form of a strip that is mounted as a cantilever to provide a free end, wherein the free end moves upon application of a driving voltage of selected voltage versus time profile to the bimorph for monotonic movement between two positions to block or unblock a light beam which propagates in a direct substantially at right angles to the plane of movement of the free end of the bimorph, said voltage versus time profile first accelerating said shutter device toward one said position and then decelerates said shutter device such that it reaches the other said position with substantially zero velocity.

19. Spectroscopy apparatus as claimed in claim 18 wherein a shutter element is affixed near to the free end of the bimorph, the shutter element having a substantially planar shape which is parallel to the plane of movement of the free end of the bimorph.

20. Spectroscopy apparatus for spectrochemical analysis of a sample comprising a light source and a system for interacting the light source and a sample for providing spectral light of the sample, and an optical system including a polychromator and a multi-element solid state detector for providing intensity measurements of the spectral light as a function of wavelength, means for serially reading a plurality of the elements of the detector to provide said light intensity measurements, a shutter device positioned such that it blocks and unblocks the spectral light adjacent to an entrance aperture of the polychromator, and a mask positioned between the shutter device and the light source for allowing only spectral light corresponding to the effective optical entrance beam of the polychromator to reach the shutter device, said shutter device having a piezoelectric structure, the shutter device being operable on application of an electrical signal of selected voltage versus time profile to the piezoelectric structure for movement between two positions, wherein at one position the spectral light is permitted to reach the detector, and at the other position the spectral light is prevented from reaching the detector for the plurality of detector elements to be serially read while the detector is shielded from the spectral light.

* * * * *